United States Patent [19]

Dimantoglou et al.

[11] Patent Number: 4,872,983

[45] Date of Patent: Oct. 10, 1989

[54] BIOCOMPATIBLE CELLULOSE DIALYSIS MEMBRANE WITH INCREASED ADSORPTION OF BETA-2-MICROGLOBULIN

[75] Inventors: Michael Dimantoglou, Erlenbach/Main; Helmut Kuhne, Kreuzau, both of Fed. Rep. of Germany

[73] Assignee: Akzo N.V., Netherlands

[21] Appl. No.: 281,762

[22] Filed: Dec. 9, 1988

[30] Foreign Application Priority Data

Dec. 11, 1987 [DE] Fed. Rep. of Germany ....... 3742072

[51] Int. Cl.$^4$ ............................................. B01D 13/00
[52] U.S. Cl. ........................... 210/500.29; 210/321.71
[58] Field of Search ................... 536/20; 210/679, 646, 210/647, 645, 649, 259, 321.71, 500.27, 500.28, 500.29, 500.3, 500.31, 500.32

[56] References Cited

U.S. PATENT DOCUMENTS

| | | | |
|---|---|---|---|
| 4,401,807 | 8/1983 | Koshugi | 536/20 |
| 4,721,730 | 1/1988 | Furuyoshi et al. | 210/679 |
| 4,770,774 | 9/1988 | Ida et al. | 210/259 |

Primary Examiner—Frank Sever
Attorney, Agent, or Firm—Oliff & Berridge

[57] ABSTRACT

A dialysis membrane for hemodialysis with improved biocompatibility is composed of a modified cellulose which has a structure represented by the formula

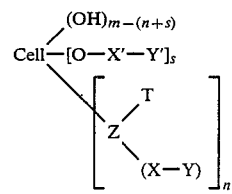

Cell is the framework of the unmodified cellulose molecule or of the chitin molecule, in each case without hydroxyl groups. Z is an atom of group V or VI (except oxygen) of the periodic system. Where Z is an atom of group V, T is a hydrogen atom or (X-Y). Where Z is an atom of group VI, T is omitted. $(n+s)$ indicates the mean degree of substitution with $0 < n < m$ and $0 \leq s < m$ and $n + s < m$. $m = 3$ in the case of the unmodified cellulose molecule and $m = 2$ in the case of the chitin molecule. -X- can be omitted as desired or -X- and -X'- denote specific divalent groups. -Y and -Y' denote -H and/or specified univalent radicals. X is identical to or different from X' and Y is identical to or different from Y'.

11 Claims, No Drawings

BIOCOMPATIBLE CELLULOSE DIALYSIS MEMBRANE WITH INCREASED ADSORPTION OF BETA-2-MICROGLOBULIN

TECHNICAL FIELD

The invention relates to a dialysis membrane for hemodialysis in the form of flat films, tubular films or hollow filaments, composed of cellulose modified by substitution.

BACKGROUND

Cellulose dialysis membranes for hemodialysis in the form of flat films, tubular films or hollow filaments have been known for a lengthy period and are still preferably employed in artificial kidneys. However, it has not yet been possible to eliminate some properties which give rise to complaints.

Thus German Pat. No. 2,705,735 discloses a dialysis membrane for hemodialysis, having antithrombogenic compounds chemically bonded thereto, the dialysis membrane consisting of two or more layers of a cellulose re-generated from cuprammonium cellulose solution, each of which has been obtained from separately fed orifices of a spinneret, which cellulose contains chemically bonded substances having antithrombogenic activity.

However, it has also been proposed in German Offenlegungsschrift No. 1,720,087 that by reacting the polymeric material of the membrane with an alkyl halide and then reacting the resulting material with an alkali metal salt of an antithrombogenic compound having a cationic residue (for example heparin or a heparinoid compound) the risk of blood coagulation is diminished. The possible alkyl halides in this context also include haloalkyldialkylamines. Moreover cellulose, but most importantly cellulose acetate, is among the possible polymers.

An antithrombogenic effect of these known dialysis membranes is observed only when the degree of substitution of the modified cellulose is high, i.e., greater than at least 0.1, and a preheparinization with a relatively high heparin concentration (0.1 to 1% by weight solutions) is carried out in a separate stage.

German Offenlegungsschrift No. 3,524,596 has already disclosed a dialysis membrane with improved biocompatibility, which is distinguished in that the mean degree of substitution of a modified cellulose is 0.02 to 0.07. The known dialysis membrane composed of modified cellulose preferably contains such a modified cellulose which has a structure represented by the formula

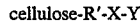
cellulose-R'-X-Y where
X represents —NR"— and/or —N+R"$_2$— and/or —S— and/or —SO— and/or —SO$_2$— and/or —CO—NR— and/or —CO—O— and/or —O—,
Y represents —R and/or —NR$_2$ and/or —Si(OR")$_3$ and/or —SO$_3$H and/or —COOH and/or —PO$_3$H$_2$ and/or —N+HR$_2$ and the salts thereof,
R' represents an alkylene group and/or cycloalkylene group and/or arylene group having a total of 1 to 25 C atoms,
R" represents a hydrogen atom or R, and
R represents an alkyl group having 1 to 5 C atoms and/or a cycloalkyl group and/or aryl group.

This known dialysis membrane is capable of reducing to a considerable extent blood coagulation, leukopenia and complement activation. However, no noteworthy extent of adsorption of beta-2-microglobulin has been detected.

Apart from the circumstance that dialysis membranes composed of synthetic or natural polymers can, when used in artificial kidneys, very easily induce blood coagulation, which is substantially prevented by appropriate drug treatment, in the case of dialysis membranes composed of regenerated cellulose there is frequently a transient fall in leukocytes in the first period of dialysis treatment when a kidney patient is treated with dialyzers having cellulose membranes. This effect is called leukopenia. Leukopenia is a reduction in the number of leukocytes (white blood corpuscles) in the circulating blood. The number of white blood corpuscles in humans is about 4,000 to 12,000 cells/mm$^3$.

Leukopenia associated with dialysis is most pronounced 15 to 20 minutes after the start, it being possible for the neutrophils (which are the leukocytes which can be stained with neutral or simultaneously with acidic and basic dyes) to disappear almost completely. Subsequently, the number of leukocytes recovers again within about one hour to almost the initial level or exceeds it.

If, after the leukocytes have recovered, a new dialyzer is connected, leukopenia occurs again to the same extent.

Cellulose membranes cause pronounced leukopenia. Even though the clinical significance of leukopenia has not been scientifically elucidated, there is nevertheless a desire for a dialysis membrane for hemodialysis which does not exhibit the leukopenic effect, without this adversely affecting the other very desired properties of dialysis membranes composed of regenerated cellulose.

During hemodialysis using membranes composed of regenerated cellulose, beside the leukopenia there has also been found a distinct complement activation. The complement system within the blood serum is a complex plasma-enzyme system which consists of many components and acts in various ways to prevent damage due to invading foreign cells (bacteria, etc.). When antibodies against the invading organism are present, there can be complement specific activation by .The complex of the antibodies with antigenic structures of the foreign cells, otherwise complement activation takes place by an alternative pathway due to special surface features of the foreign cells. The complement system is based on a multiplicity of plasma proteins. After activation, these proteins react specifically in a defined sequence with one another and, finally, a cell-damaging complex which destroys the foreign cell is formed.

Individual components release peptides which induce inflammatory manifestations and occasionally can also have undesired pathological consequences for the organism. It is assumed that in the case of hemodialysis membranes composed of regenerated cellulose the activation takes place by the alternative pathway. These complement activations are detected objectively by determination of the complement fragments C3a and C5a.

In this context, reference is made to the following studies: D. E. Chenoweth et al., Kidney International vol. 24, pages 746 et seq., 1983 and D. E. Chenoweth, Asaio-Journal vol. 7, pages 44 et seq., 1984.

The carpal tunnel syndrome is but little affected by the known modified dialysis membranes. This is why there is a considerable need for further modifications of the cellulose in order to eliminate this phenomenon too.

SUMMARY OF THE INVENTION

An object of the present invention was to provide dialysis membranes for hemodialysis in the form of flat films, tubular films or hollow filaments, composed of cellulose modified by substitution, which have optimum properties in terms of leukopenia, complement activation and blood coagulation, and, furthermore, are able to absorb to a considerable extent the beta-2-microglobulin which is responsible for the carpal tunnel effect and thus also to suppress the adverse effect on hemodialysis. This and other objects are achieved by a dialysis membrane formed of a modified cellulose.

DETAILED DESCRIPTION OF PREFERRED EMBODIMENTS

The modified cellulose of the invention has a structure represented by the formula

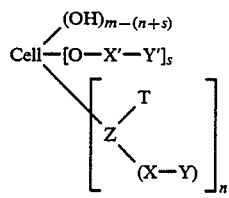

The lowermost substituent can also be referred to as $A_n$, and the group (X–Y) can also be referred to as B. In this formula, Cell is the framework of the unmodified cellulose molecule or of the chitin molecule, in each case without hydroxyl groups. Z is an atom of group V or VI (except oxygen) of the periodic system. When Z is an atom of group V, T denotes a hydrogen atom or (X-Y). When Z is an atom of group VI, T is omitted. (n+s) indicates the mean degree of substitution with $0 < n < m$ and $0 \leq s < m$ and $n+s < m$. $m=3$ in the case of the unmodified cellulose molecule and $m=2$ in the case of the chitin molecule.

—X— can be omitted or —X— and —X'— denote an alkylene, alkenylene or alkynylene radical which may or may not be substituted (straight-chain and/or branched, the carbon chain also being able to be interrupted by hetero atoms such as O, S, N, P or Si as well as by CO—, CONR— or COO— groups) and/or a cycloalkylene (which may or may not contain hetero atoms and/or may or may not be substituted) and/or arylene and/or arylalkylene and/or arylalkenylene and/or arylalkynylene (which may or may not contain hetero atoms and/or may or may not be substituted) and/or bisarylalkylene and/or bisarylene radical (which may or may not be substituted) and/or radical of a condensed aromatic compound (which may or may not be substituted) and/or radical of a heterocyclic compound (which may or may not be substituted).

—Y and —Y' denote —H, and/or —NR$_2$, and/or —N$^+$R$_3$, and/or —COOH or a salt thereof, and/or —COOR, and/or —CONR$_2$, and/or —CO— , R, and/or —CS—R, and/or —CSOH or a salt thereof, and/or —CSOR, and/or —CSNR$_2$, and/or —SO$_3$H or a salt thereof, and/or —SO$_3$R, and/or —SO$_2$—R, and/or —SO$_2$NR$_2$, and/or —SR, and/or —SOR, and/or —SONR$_2$, and/or —PO$_3$H$_2$ or a salt thereof, and/or —PO(OR)$_2$, and/or -PO2H(NR2), and/or -PO(NR2)2, and/or -PO2H2, and/or -POH(OR), and/or —CN, and/or —NO$_2$, and/or —OR, and/or halogen, and/or —Si(OR)$_3$.

R denotes a hydrogen atom and/or an alkyl, alkenyl or alkynyl group, which may or may not be substituted, having 1 to 36 C atoms (straight-chain and/or branched, the carbon chain also being able to be interrupted by hetero atoms such as O, S, N, P or Si as well as by CO—, CONR— or COO— groups) and/or a cycloalkyl (which may or may not contain hetero atoms and/or may or may not be substituted) and/or aryl and/or arylalkyl and/or arylalkenyl and/or arylalkynyl (which may or may not contain hetero atoms and/or may or may not be substituted) and/or bisarylalkyl and/or bisaryl radical (which may or may not be substituted) and/or radical of a condensed aromatic compound (which may or may not be substituted) and/or radical of a heterocyclic compound (which may or may not be substituted).

X is identical to or different from X' and Y is identical to or different from Y'.

Whereas unmodified cellulose contains 3 hydroxyl groups available for substitution, in the case of chitin there has already been substitution of one hydroxyl group by acetamide groups. This substitution is no longer considered as contributing to the mean degree of substitution within the scope of the present invention, provided modified celluloses based on the chitin molecular framework are employed.

The dialysis membranes according to the invention can be adjusted to the desired degree of substitution by mixing substituted cellulose with unmodified cellulose. The substitution is carried out by processes known per se. Preferably the degree of substitution n is equal to 0.003 to 2.6. Especially preferred are such dialysis membranes in which the degree of substitution n is equal to 0.005 to 0.95. The degree of substitution s is preferably equal to 0 to 0.5 n.

The process described in U.S. Pat. 3,702,754 is also suitable if care is taken that degradation is limited. When crosslinking takes place in this process, some of the products are insoluble in the known cellulose solvents, for example cuprammonium solution, which then makes them unsuitable for the dialysis membrane according to the invention.

However, other known processes have proved to be more suitable For example, it is possible in this connection to refer to the Journal of Polymer Science - Part C, No. 11 (1965) pages 107–118 or J. Am. Chem. Soc., Feb. 1950, pages 670—674 and to "Cellulose and Cellulose Derivatives" Part II, edited by Ott, Spurlin and Grafflin, Interscience Publishers, Inc., New York, nd edition, 1954, page 822. In these processes, the degree of substitution is adjusted to any desired level.

The complement activation within the scope of the present invention was assessed on the basis of the C3a or C5a fragments. For this purpose, 300 ml of heparinized blood plasma was recirculated in vitro through a dialyzer with an effective exchange area of 1 m$^2$ at a plasma flow rate of 100 ml/min for a period of 4 hours. The C3a fragments in the plasma were determined using the RIA method (Upjohn assay). The relative complement activation for the particular time of measurement was calculated as a percentage by forming the ratio of the concentration at the time of sampling with the initial value. The measurement after a recirculation time of 4 hours was used for the evaluation. Flat membranes are incubated with heparinized blood plasma for 3 hours and then the C3a fragments are determined. The C5a fragments were determined analogously.

The increase in the beta-2-microglobulin level in longterm dialysis patients is observed after use of membranes composed of regenerated cellulose and is attributed to these membranes being less permeable to substances in the molecular weight range 1,000 to 20,000 and the latter thus being removed to an insufficient extent during the dialysis. Beta-2-microglobulin is not adsorbed to a noteworthy extent onto customary membranes composed of regenerated cellulose. However, the cellulose derivatives according to the invention can contribute in an unexpected manner to this.

The beta-2-microglobulin content adsorbed onto the membrane is measured within the scope of the invention in the following manner.

10 ml of human blood plasma are added to each 500 mg of substance (dialysis membrane) and incubated at 37° C. for 30 minutes. The human blood plasma contains 13.67 mg/liter of beta 2-microglobulin. The sample is centrifuged at 3,000 r.p.m. for 15 minutes. The beta-2-microglobulin content in the supernatant is determined. The sample is then washed 2 times with 10 ml of phosphate-buffered saline each time. The microglobulin content in the washings is also determined. The percentage amount of beta-2-microglobulin adsorbed can be calculated from the difference between the original and the unabsorbed beta-2microglobulin.

The average degree of polymerization (DP) was determined in a cupriethylenediamine solution by the DIN 54270 method.

The degree of etherification and/or degree of esterification were determined on the basis of the analytical results which are known and typical for the substituents, for example nitrogen by the Kjeldahl method, sulfur by the Schoniger method or phosphorus by the molybdate method, where appropriate from the difference between before and after saponification.

The modified cellulose corresponding to the structural formula indicated above is preferably one in which Z represents a nitrogen or a sulfur atom.

Very suitable dialysis membranes are obtained in the case of modified celluloses which are based, as desired, on substituted X and X' molecular residues when X and X' are substituted by the molecular residues Y and Y' respectively.

In general, preferred dialysis membranes are those in which the substituents Y and Y' are secondary, tertiary or quaternary amino groups and/or carboxy groups and/or sulfo groups and/or phosphonato groups and/or silicato groups.

Good results in terms of the desired biocompatibility are obtained with dialysis membranes which contain modified cellulose in which, in the indicated structural formula, (X–Y) denotes dialkylaminoalkylene and/or carboxylalkylene and/or carboxylarylalkylene and/or sulfoalkylene and/or sulfoarylalkylene and/or phosphonatoalkylene and/or phosphonatoarylalkylene.

Another embodiment of the invention is obtained when (X–Y) denotes silicatopropylene.

Preferred alkyl radicals for R are methyl groups and/or ethyl groups and/or propyl groups.

Dialysis membranes composed of cellulose regenerated from cuprammonium solutions have, because of their high level of development, been of use for many years.

However, it is possible within the scope of the invention and without restriction to carry out the regeneration from other cellulose solvents, for example from dimethyl acetamide/LiCl or from tertiary amine oxides/water or even from viscose solutions. Modified celluloses having a chitin molecular framework cannot, given their insolubility, be regenerated from cuprammonium solutions. However, this is possible without problems from the other mentioned solvents for cellulose.

EXAMPLE 1

A) Reaction of cellulose with p-toluenesulfonyl chloride 486 g (3 mole) of cellulose (DP = 1400, measured in cupriethylenediamine as solvent) were suspended in 6,000 ml of pyridine (anhydrous) in a 10 liter flask. Then 171.45 g (0.9 mole) of p-toluenesulfonyl chloride were added, and the mixture was stirred at 25° C. for 48 hours. The reaction product was filtered off with suction, washed successively with ethanol, water and ethanol and dried in a vacuum oven at 65° C. This resulted in 565 g of a product having a sulfur content of 3.03%, corresponding to a degree of esterification of 0.18.

B) Reaction of cellulose toluenesulfonate ester with 2-mercaptosuccinic acid 150 ml of ethanol and 27 g (0.18 mole) of 2mercaptosuccinic acid were introduced into a mixer and neutralized with a solution of 50.4 g (0.90 mole) of potassium hydroxide in 150 ml of water. Then 189.72 g (1 mole) of the ester previously obtained (Example 1A) were added, and the mixture was heated at 80° C. for 18 hours. The resulting product was washed with water, aqueous hydrochloric acid solution and ethanol and dried in a vacuum oven at 65° C. This resulted in 173 g of a product with a sulfur content of 1.65%, corresponding to a DS (n) of 0.09.

A customary procedure was used to prepare a cuprammonium solution from this cellulose derivative, containing 9% of cellulose derivative, and to spin it to give capillary membranes.

The cellulose membranes obtained in this way had the following properties:

| | |
|---|---|
| Wall thickness | 10 μm |
| Internal diameter | 200 μm |
| Ultrafiltration rate | 4.6 ml/h · m$^2$ · mm Hg at 37° C. |
| Vitamin B12 permeability | 4.9 × 10$^{-3}$ cm/min at 37° C. |
| Beta-2-microglobulin adsorption | 35% |

The complement activation with the above-mentioned cellulose derivative membrane is less than that with unmodified cellulose membranes. The reduction in C3a compared with the unmodified cellulose membrane is 96%.

EXAMPLE 2

54 g (0.72 mole) of aminoacetic acid and 200 ml of water were introduced into a mixer. The amino acid was neutralized with a solution of 50.4 g (0.9 mole) of potassium hydroxide in 100 ml of water, and then 189.72 g (1 mole) of the ester from Example 1A were added, and the mixture was heated at 80° C. for 18 hours. The reaction product was washed with water and ethanol and dried in a vacuum oven at 65° C.

Yield: 167 g
N Content: 0.7%
Degree of substitution (n): 0.085

The capillary membranes prepared from a cuprammonium solution by customary procedure had the following properties:

| | |
|---|---|
| Wall thickness | 11 μm |
| Internal diameter | 205 μm |
| Ultrafiltration rate | 4.1 ml/h · m² · mm Hg at 37° C. |
| Vitamin B12 permeability | 4.5 × 10⁻³ cm/min at 37° C. |
| Beta-2-microglobulin adsorption | 28% |

The reduction in C3a compared with the unmodified cellulose membrane is 92%. EXAMPLE 3

In analogy to Example 1A, diethylaminoethylcellulose p-toluenesulfonate ester was prepared by reaction of p-toluenesulfonyl chloride with diethylaminoethylcellulose with a low degree of substitution, and had the following specification.

Degree of etherification (s): 0.04
Degree of esterification: 0.10

By reaction of the ester with 3-mercaptopropionic acid in the presence of KOH in analogy to Example 1B, there was obtained a cellulose derivative with an S content of 0.94% (n=0.05) and an N content of 0.3% (s=0.037).

The capillary membranes prepared from a cuprammonium solution by customary procedure had the following properties:

| | |
|---|---|
| Wall thickness | 14 μm |
| Internal diameter | 205 μm |
| Ultrafiltration rate | 4.2 ml/h · m² · mm Hg at 37° C. |
| Vitamin B12 permeability | 4.8 × 10⁻³ cm/min at 37° C. |
| Beta-2-microglobulin adsorption | 40% |

The reduction in C3a compared with the unmodified cellulose is 98%.

EXAMPLES 4-9

The derivatives listed in Table 1 were prepared in analogy to Example 1 or Example 2, processed by known procedure to obtain flat membranes and examined.

EXAMPLE 10

36.8 g (0.4 mole) of thioglycolic acid were introduced into a mixer and neutralized with a solution of 44.8 g (0.8 mole) of potassium hydroxide in 60 ml of water. Then 37.94 g (0.2 mole) of the ester from Example 1A were added, and the mixture was heated at 70° C. for 24 hours. The reaction product was washed with water and ethanol and dried in a vacuum oven at 65° C. This resulted in 32.7 g of a product with a potassium content of 2.09%, corresponding to a DS (n) of 0.093.

A customary procedure was used to prepare a cuprammonium solution from this cellulose derivative, containing 9% of cellulose derivative, and to process it to obtain flat membranes.

The reduction in C5a compared with unmodified cellulose is 99%.

EXAMPLE 11-20

In analogy to Example 1, 2, 3, or 10, the derivatives listed in Table 2 were synthesized and processed by known procedures to flat membranes, and their complement activation was determined on the basis of the C5a fragments.

TABLE 1

| Example | Starting polymer | s | X' | Y' | Z | T | X | Y | n | C3a red. | Beta mic glob ads. % |
|---|---|---|---|---|---|---|---|---|---|---|---|
| 4 | Cellulose | — | — | — | S | — | $CH_2$ | COOH | 0.12 | 94 | 25 |
| 5 | Cellulose | — | — | — | S | — | $C_2H_4$ | $SO_3H$ | 0.07 | 96 | 33 |
| 6 | Cellulose | 0.03 | $C_2H_4$ | $SO_3H$ | N | H | $CH_2$ | COOH | 0.04 | 98 | 43 |
| 7 | Cellulose | — | — | — | N | H | $(CH_3)_2C_2H_2$ | COOH | 0.06 | 89 | 32 |
| 8 | Cellulose | 0.04 | $C_2H_4$ | $SO_3H$ | S | — | $CH_2$ | COOH | 0.09 | 99 | 56 |
| 9 | Chitin | — | — | — | S | — | $CH_2$ | COOH | 0.13 | 87 | 47 |

TABLE 2

| Example | Starting polymer | s | X-Y | Z | T | X'-Y' | n | C5a red. % |
|---|---|---|---|---|---|---|---|---|
| 11 | Cellulose | — | — | S | — | $CH_2$—COOH | 0.03 | 98 |
| 12 | Cellulose | — | — | S | — | $C_6H_{13}$ | 0.30 | 90 |
| 13 | Cellulose | — | — | S | — | $C_6H_5$ | 0.20 | 70 |
| 14 | Cellulose | — | — | S | — | $C_2H_4$—OH | 0.15 | 65 |
| 15 | Cellulose | — | — | S | — | $C_3H_6$—$SO_3H$ | 0.06 | 87 |
| 16 | Cellulose | — | — | N | H | $C_6H_3$(—OH)—COOH | 0.10 | 92 |
| 17 | Cellulose | 0.05 | $N(i-C_3H_7)_2$ | S | — | $CH_2COOH$ | 0.08 | 100 |
| 18 | Cellulose | 0.07 | $C_5H_{10}N$ | N | H | CH(—COOH)—$C_6H_5$ | 0.03 | 100 |
| 19 | Cellulose | 0.12 | $C_4H_8$—$SO_3H$ | S | — | $C_{12}H_{25}$ | 0.02 | 95 |
| 20 | Cellulose | 0.08 | $C_7H_{15}$—COOH | S | — | $C_6H_5$ | 0.03 | 90 |

What is claimed is:

1. A dialysis membrane for hemodialysis in the form of flat films, tubular films or hollow filaments, composed of substitution-modified cellulose, wherein the modified cellulose has a molecular structure which substantially adsorbs beta-2-microglobulin present in blood plasma and is effective to reduce carpal tunnel syndrome and is represented by the formula

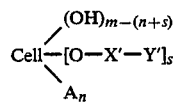

wherein:

Cell is a framework of an unmodified cellulose molecule or of a chitin molecule, in each case without hydroxyl groups;

A is selected from the group consisting of and Z-B;

Z is an atom of group V or VI or the Periodic System other than oxygen;

In the case where Z is an atom of group V, A is and T is a hydrogen atom or (X-Y); in the case where Z is an atom of group VI, A is (n+s) is the mean degree of substitution; $0<n<m$ and $0 \leq s<m$ and $n+s<m$;

m=3 in the case of the unmodified cellulose molecule and m=2 in the case of the chitin molecule;

B is selected from the group consisting of Y and X-Y;

—X— and —X'— are each at least one member selected from the group consisting of a substituted or unsubstituted, straight or branched chain alkylene, alkenylene or alkynylene radical in which the carbon chain may be interrupted by hetero atoms or be CO—, CONR— or COO—groups, a substituted or unsubstituted cycloalkylene which may contain hetero atoms, a substituted or unsubstituted arylene, arylalkylene, arylalkenylene or arylalkynlene radical which may contain hetero atoms, a substituted or unsubstituted bisarylalkylene or bisarylene radical, a substituted bisarylalkylene or bisarylene radical of a condensed aromatic compound, and a substituted or unsubstituted readical of a heterocyclic compound;

—Y and —Y' are each at least one member selected from the group consisting of —H, —NR₂ —N⁺R₃, —COOH or a salt thereof, —COOR, —CONR₂, —CO—R, —CS—R, —CSOH or a salt thereof, —CSOR, —CSNR₂, —SO₃H or a salt thereof, —SO₃R, —SO₂R, —SO₂NR₂, —SR, —SOR, —SON R₂, —PO₃H₂ or a salt thereof, —PO(OR)₂, —PO₂H(NR₂), —PO(NR₂)₂, —PO₂H₂, —PO-H(OR), —CN, —NO₂, —OR, halogen and Si-(OR)₃;

R is at least one member selected from the group consisting of a hydrogen atom, a straight or branched chain alkyl, alkenyl or alkynyl group having 1 to 36 atoms in which the carbon chain may be interrupted by hetero atoms or by CO—, CONR— or COO— groups, a substituted or unsubstituted cycloalkyl group which may contain hetero atoms, a substituted or unsubstituted aryl, arylalkyl, arylalkenyl or arylalkynyl radical which may contain hetero atoms, a substituted or unsubstituted bisarylalkyl or bisaryl radical, a substituted or unsubstituted radical or a condensed aromatic compound, and a substituted or unsubstituted radical of a heterocyclic compound;

X is identical to or different from X' and Y is identical to or different from Y'.

2. A dialysis membrane as claimed in claim 1, wherein n=0.003-2.6.

3. A dialysis membrane as claimed in claim 2, wherein n =0.005 to 0.95.

4. A dialysis membrane as claimed in claim 1, where s =0 to 0.5 n.

5. A dialysis membrane as claimed in claim 1, wherein Z is a nitrogen or a sulfur atom.

6. A dialysis membrane as claimed in claim 1, wherein X or X' is substituted with the molecular radicals Y or Y'.

7. A dialysis membrane as claimed in claim 1, wherein the modified cellulose contains at least one member selected from the group consisting of secondary, tertiary and quaternary amino groups, carboxy groups, sulfo groups, phosphonato groups and silicato groups.

8. A dialysis membrane as claimed in claim 7, wherein X-Y is at least one member selected from the group consisting of dialkylaminoalkylene, carboxyalkylene, carboxyarylalkylene, sulfurfoalkylene, sulfoarylalkylene, phosphonatoalkylene and phosphonatoarylalkylene.

9. A dialysis membrane as claimed in claim 1, wherein X-Y is silicatopropylene.

10. A dialysis membrane as claimed in claim 1, wherein said alkyl group is at least one member selected from the group consisting of ethyl, methyl and propyl.

11. A dialysis membrane as claimed in claim 1, wherein said hetero atoms are at least one number selected from the group consisting of O, S, N, P and Si.

* * * * *

UNITED STATES PATENT AND TRADEMARK OFFICE
CERTIFICATE OF CORRECTION

PATENT NO. : 4,872,983

DATED : October 10, 1989

INVENTOR(S) : Michael DIAMANTOGLOU et al

It is certified that error appears in the above-identified patent and that said Letters Patent is hereby corrected as shown below:

ON THE FIRST PAGE OF THE PATENT:

In INID Code 75, change "Dimantoglou" to --Diamantoglou--.

IN THE SPECIFICATION:

Col. 1, line 24, change "re-generated" to --regenerated--;

line 61, change "-O-" to ---O---.

Col. 2, line 48, change "complement specific" to --complement-specific--; after "by" delete "."; change "The" to --the--.

Col. 4, line 2, change "-PO2H(NR2), and/or -PO(NR2)2" to ---$PO_2H(NR_2)$, and/or -$PO(NR_2)_2$--;

line 3, change "-PO2H2," to ---$PO_2H_2$,--;

line 55, change "nd" to --2nd--.

Col. 6, line 31, change "2mercap-" to --2-mercap- --;

line 60, delete "EXAMPLE 2";

between lines 60 and 61, insert --EXAMPLE 2--.

UNITED STATES PATENT AND TRADEMARK OFFICE
CERTIFICATE OF CORRECTION

PATENT NO. : 4,872,983
DATED : October 10, 1989
INVENTOR(S) : Michael DIAMANTOGLOU et al It is certified that error appears in the above-identified patent and that said Letters Patent is hereby corrected as shown below:

Col. 7, line 16, delete "EXAMPLE 3";

between lines 16 and 17, insert --EXAMPLE 3--.

Col 8, in Table 2, Example 19, change "95" to --85--.

IN THE CLAIMS:

Claim 1, col. 9, line 12, after "of" insert $--Z\genfrac{}{}{0pt}{}{T}{B}--$;

line 14, change "or" (second occurrence only) to --of--.

line 16, after "is" (second occurrence only) insert $--Z\genfrac{}{}{0pt}{}{T}{B}--$;

line 18, after "is" (second occurrence only) insert --Z-B;--;

line 37, after "substituted" insert --or unsubstituted--; delete "bisarylalkylene or bisarylene";

UNITED STATES PATENT AND TRADEMARK OFFICE
CERTIFICATE OF CORRECTION

PATENT NO. : 4,872,983

DATED : October 10, 1989

INVENTOR(S) : Michael DIAMANTOGLOU et al

It is certified that error appears in the above-identified patent and that said Letters Patent is hereby corrected as shown below:

line 39, change "readical" to --radical--;

line 41, change "Y·" to --Y'--;

line 47, change "-SON R$_2$," to ---SONR$_2$,--.

Claim 1, col. 10, line 6, after "36" insert --C--;

line 14, change "or" (second occurrence only) to --of--;

Claim 8, col. 10, line 38, change "sulfurfoalkylene" to --sulfoalkylene--.

Claim 11, col. 10, line 47, change "number" to --member--.

Signed and Sealed this

Twenty-fifth Day of December, 1990

Attest:

HARRY F. MANBECK, JR.

*Attesting Officer*     *Commissioner of Patents and Trademarks*